(12) United States Patent  
Bon

(10) Patent No.: US 6,599,265 B2
(45) Date of Patent: Jul. 29, 2003

(54) BRAKE ASSEMBLY FOR A STEERABLE CATHETHER

(75) Inventor: Edwin Bon, Canton, GA (US)

(73) Assignee: Visionary Biomedical, Inc., Roswell, GA (US)

( * ) Notice: Subject to any disclaimer, the term of this patent is extended or adjusted under 35 U.S.C. 154(b) by 0 days.

(21) Appl. No.: 09/897,695

(22) Filed: Jul. 2, 2001

(65) Prior Publication Data

US 2002/0019591 A1 Feb. 14, 2002

Related U.S. Application Data

(60) Provisional application No. 60/216,047, filed on Jul. 5, 2000.

(51) Int. Cl.[7] ............................................. A61M 37/00
(52) U.S. Cl. ................................ 604/95.01; 604/95.04; 604/95.02
(58) Field of Search .............................. 604/528, 95.01, 604/95.04, 95.05, 95.02, 95.03; 188/166, 167, 168, 169, 14, 20, 21

(56) References Cited

U.S. PATENT DOCUMENTS

| 1,872,146 A | * | 2/1932 | Jackson | ...................... 188/20 |
|---|---|---|---|---|
| 5,199,950 A | | 4/1993 | Schmitt et al. | |
| 5,328,467 A | * | 7/1994 | Edwards et al. | .......... 604/95.01 |
| 5,454,794 A | | 10/1995 | Narciso, Jr. et al. | |
| 5,456,664 A | | 10/1995 | Heinzelman et al. | |
| 5,526,820 A | | 6/1996 | Khoury | |
| 5,531,687 A | | 7/1996 | Snoke et al. | |
| 5,658,263 A | | 8/1997 | Dang et al. | |
| 6,123,699 A | * | 9/2000 | Webster, Jr. | ................. 604/528 |
| 6,203,525 B1 | * | 3/2001 | Whayne et al. | .............. 604/528 |
| 6,213,974 B1 | | 4/2001 | Smith et al. | |
| 2001/0037084 A1 | * | 11/2001 | Nardeo | ..................... 604/95.04 |

* cited by examiner

Primary Examiner—Michael J. Hayes
Assistant Examiner—Matthew DeSanto
(74) Attorney, Agent, or Firm—Gardner Groff, P.C.

(57) ABSTRACT

A brake assembly for a steerable catheter that allows both dynamic locking and swapping between a locked mode of operation and an unlocked mode of operation is described. Dynamic locking enables fine adjustment of the catheter shaft position, while swapping between modes results in a more multipurpose catheter. Generally, the brake assembly includes a brake shoe positioned for slidable movement between a locked position contacting the steering dial and an unlocked position not contacting the steering dial. At least one spring biases the brake shoe toward the locked position. A catheter including a brake assembly is also described.

14 Claims, 4 Drawing Sheets

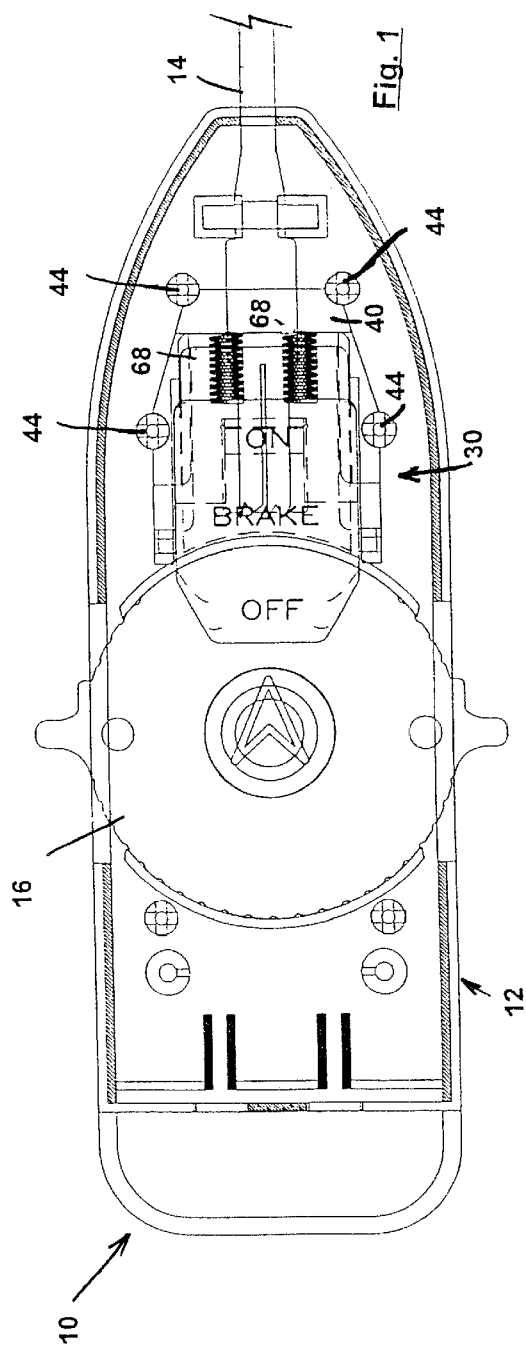
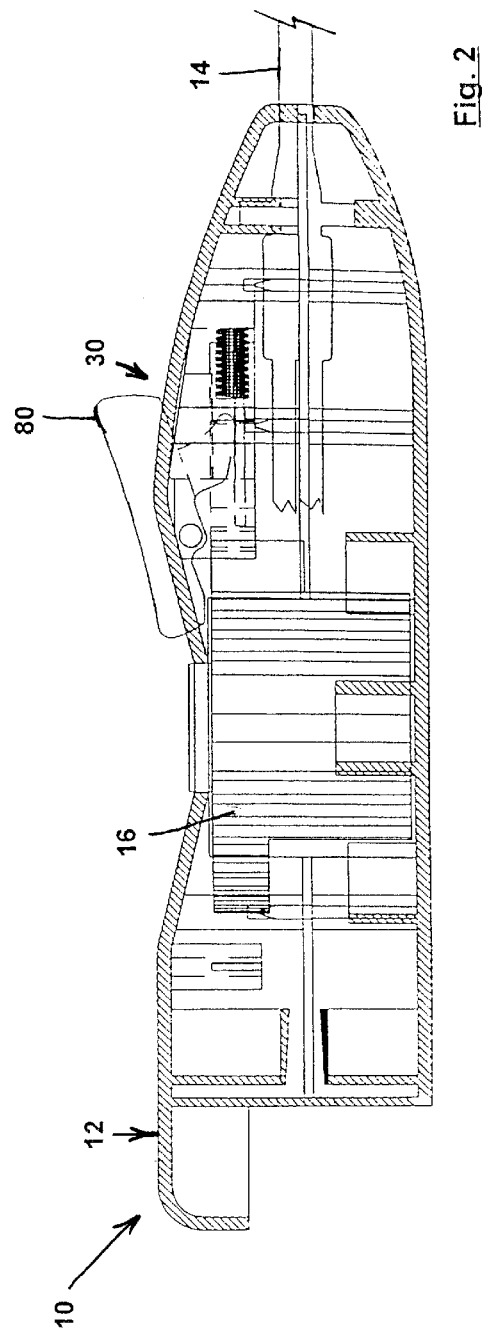

BRAKE ASSEMBLY FOR A STEERABLE CATHETHER

CROSS REFERENCE TO RELATED APPLICATIONS

This patent application claims priority to commonly-owned U.S. Provisional Patent Application with Ser. No. 60/216,047 filed on Jul. 5, 2000, which is incorporated herein by reference.

BACKGROUND OF THE INVENTION

1. Field of the Invention

The present invention relates generally to medical devices, and more particularly to a brake assembly for a steerable catheter that allows both dynamic locking and swapping between a locked mode of operation and an unlocked mode of operation.

2. Description of Related Art

Medical practitioners frequently use catheters to access internal regions of a patient's body for a variety of medical procedures. The use of catheters advantageously reduces or eliminates the need for more invasive procedures. Medical catheters may be used to access internal body regions with a fiberoptic scope, light bundles, and/or other surgical instruments or devices, for a variety of diagnosis, treatment and/or material delivery purposes. For example, U.S. Pat. No. 5,658,263 to Dang, et al. discloses a multi-segmented guiding catheter typically utilized for internal vascular access.

Steerable catheters have been developed to provide improved access to internal tissue. These catheters typically include a flexible catheter shaft and steering wires or other steering means for controlling the flexure of the catheter shaft. An example of a steerable catheter is shown by U.S. Pat. No. 5,199,950 to Schmitt, et al. U.S. Pat. No. 5,454,794 to Narcisco, et al. shows a steerable light-diffusing catheter for treating luminal surfaces with photodynamic therapy. A mechanism for steering a catheter is disclosed by U.S. Pat. No. 5,456,664 to Heinzelman, et al.

For certain applications, it has been found desirable by some practitioners to provide a steerable catheter with a locking steering mechanism. As the steering mechanism flexes the catheter shaft, the locking mechanism retains the shaft in the selected flexed position even after the steering dial is released. This can be accomplished, for example, by providing ridges or notches on the outer circumferential face of the steering dial, and providing a spring actuated pawl or other retaining element for engagement with the ridges or notches.

These locking steering mechanisms suffer the disadvantage that the steering mechanism locks only in discrete, spaced-apart positions, typically corresponding to the spaced ridges or notches on the outer circumferential face of the steering dial. Adjacent locking positions may be further apart than would be desirable to the practitioner. Thus, it has been found that a need exists for a fully adjustable steering lock mechanism that permits the user to lock the catheter shaft in any position within a continuous range.

Although locking steering mechanisms are often desirable, it is sometimes preferable to have a freewheeling steering mechanism that does not lock the shaft in position, but instead permits the catheter shaft to return to a generally straight configuration when the steering dial is released. Previously known locking steering mechanisms typically cannot convert into freewheeling mechanisms, which implicitly limits use to applications where freewheeling is not desired. It has therefore been discovered that needs exist for a steerable catheter having a steering mechanism that permits the practitioner to selectively engage or disengage a steering brake assembly. Further needs exist for a catheter whereby the user can choose to retain the shaft in a selected flexed position by locking the steering mechanism after releasing the steering dial, or alternatively, can allow freewheeling of the steering dial such that the catheter shaft returns to a generally straight configuration when the steering dial is released.

It is to the provision of a steerable catheter and steering brake assembly meeting these and other needs that the present invention is primarily directed.

SUMMARY OF THE INVENTION

Briefly described, in a preferred form, the present invention is a brake assembly for a steerable catheter that allows both dynamic locking and swapping between a locked mode of operation and an unlocked mode of operation. Dynamic locking enables very fine adjustment of the catheter shaft position, and locking of the shaft in an infinite number of positions through the entire range of motion of the catheter shaft. This advantageously frees the user from maintaining torque on the steering dial to maintain catheter tip positioning. Consequently, the user can concentrate on diagnosis, avoid hand fatigue, and use the hands for other tasks.

In addition to dynamic locking, preferred forms of the present invention allow swapping between a locked mode of operation and an unlocked mode of operation. Thus, a user can either lock the catheter shaft in a given position or allow freewheeling. During freewheeling, the catheter returns to a generally straight position after a user releases the steering dial. As a result, a user can more effectively redirect the direction of the catheter for further investigation. Thus, the invention also advantageously improves stability of catheter shaft positioning, which improves imaging and recording. Moreover, swapping between modes of operation results in a more multi-purpose catheter that can be used in both environments where locking catheters are needed as well as environments where non-locking catheters are needed.

In one preferred form, the invention is a brake assembly for dynamically locking a steerable catheter having a steering dial rotatable through a plurality of positions. The brake assembly comprises a brake shoe positioned for slidable movement between a locked position contacting the steering dial and an unlocked position not contacting the steering dial. At least one spring biases the brake shoe toward the locked position.

In another preferred form, the invention is a brake assembly for dynamically locking a steerable catheter having a steering dial rotatable through a plurality of positions. The brake assembly comprises a base assembly connected to the catheter and positioned proximate the steering dial. A spring-biased brake shoe is positioned in sliding relation to the base assembly and movable between a locked position engaging the steering dial and an unlocked position not engaging the steering dial. A toggle is pivotally connected to the base assembly and movable between a first position corresponding to the locked position of the brake shoe and a second position corresponding to the unlocked position of the brake shoe.

In another preferred form, the invention is a steerable catheter that comprises a catheter body, a flexible catheter shaft extending from the catheter body, and a steering dial rotationally mounted to the catheter body for manipulating the shaft. A brake assembly is also included. The brake assembly comprises a base assembly connected to the catheter body and positioned proximate the steering dial. A brake shoe is positioned in sliding relation to the base assembly and having a contact face slidably mounted to the catheter for selectively engaging and disengaging with the steering dial. The brake assembly further comprises at least one spring for biasing the contact face of the brake shoe against the steering dial.

In yet another preferred form, the invention is a steerable catheter comprising a housing, a flexible shaft extending from the housing, a steering dial for steering the shaft, and a brake assembly. The brake assembly preferably comprises a brake element frictionally engaged between the steering disc and the housing. In one embodiment of the invention, the brake element is a brake sleeve frictionally engaged between a socket in the housing and a boss on the steering dial. In another embodiment, the brake element is a brake shoe biased into frictional engagement with a face of the steering dial.

These and other features and advantages of preferred forms of the present invention are described herein with reference to the drawing figures.

BRIEF DESCRIPTION OF THE DRAWING FIGURES

FIG. 1 is a top cutaway view of a steerable catheter that includes a brake assembly according to a preferred form of the present invention.

FIG. 2 is a side cutaway view of the steerable catheter body with the brake assembly shown in FIG. 1.

DETAILED DESCRIPTION

Figure 3:
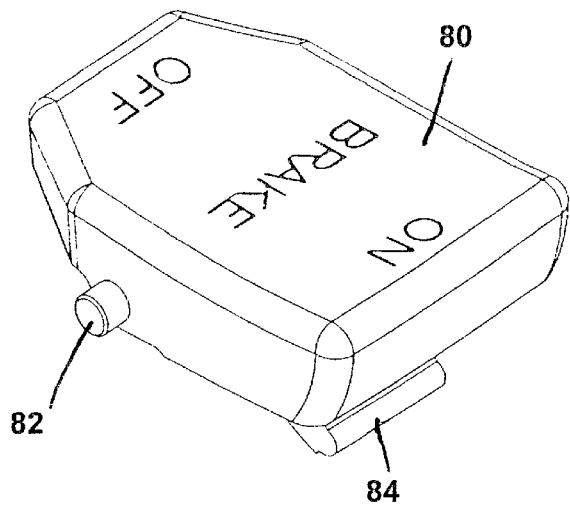
FIG. 3 is a perspective view illustrating a base assembly for the brake assembly shown in FIG. 1.

Referring now to the figures, in which like numerals refer to like elements through the several figures, FIG. 1 is a top cutaway view of a steerable catheter that includes a brake assembly. The catheter 10 includes a catheter body 12 and a steerable catheter shaft 14. Though not shown in FIG. 1, the catheter body 12 preferably includes upper and lower half housings. Consequently, the shaft 14 is preferably secured within a recess formed between the upper and lower housing members. Typically, the recess and hence the catheter shaft 14 extend from one end of the body 12. The catheter shaft 14 preferably is any one of various types of flexible catheter shafts, such as the catheter shaft disclosed in U.S. Pat. No. 6,213,974 to Smith, which patent is hereby incorporated herein by reference.

Typically, steering wires extend through the shaft 14 and connect to a steering dial 16. As mentioned above, upper and lower half housing members preferably secure the steering dial 16 therebetween. The steering dial 16 is rotationally mounted within the catheter body 12 and coupled to the steering wires such that rotation of the steering dial 16 clockwise correspondingly flexes the shaft 14 to the right, and counterclockwise rotation of the dial flexes the shaft to the left. For example, rotating the steering dial 16 flexes the catheter shaft 14 to the right. Thus flexibility of the catheter shaft 14 and the rotational limits of the steering dial 16 jointly define the range of motion of the catheter shaft 14.

FIG. 1 also illustrates that the catheter 10 includes a brake assembly 30 according to one form of the present invention. As more clearly seen in FIG. 2, the brake assembly 30 preferably includes a toggle 80, which is described in detail with reference to FIG. 5. However, the design of the catheter body 12 ergonomically positions both steering dial 16 and toggle 80 within easy reach of the user. Consequently, effective single-handed operation of the catheter 10 is achieved.

The components of the brake assembly 30 are shown in greater detail in FIGS. 3–7. FIG. 3 is a perspective view illustrating a base assembly 40 for the brake assembly shown 30. The base assembly 40 is mounted to the catheter body 12 adjacent to the steering dial 16. The base assembly 40 can be attached to the catheter body 12 by adhesive, fasteners, or integrally forming the base 40 with the body 12. Alternatively or in addition, recesses 42 formed in the base 40 can engage bosses 44 (see FIG. 1) of the catheter body 12.

As shown in FIG. 3, the base assembly 40 resembles a generally U-shaped yoke. Alternatively, this base assembly could be V-shaped, arced, or some other suitable shape. The base assembly preferably comprises an end piece 46, and a first arm 48 and a second arm 50 that extend from opposite ends of end piece 46. Each of these arms includes an inwardly projecting rib 52 that extends lengthwise along its inner face and away from the end piece 46. In addition, each of the arms 48, 50 also defines an opening 54 distal the end piece 46. Though not shown, the end piece 46 can include one or more recesses or projections on the inner face of for retaining springs 68, which are described with reference to FIG. 4. Using the projecting rib 52, opening 54 and recesses (not shown), the base assembly effectively and securely couples with the other components of the brake assembly 30, as described below.

Figure 4:
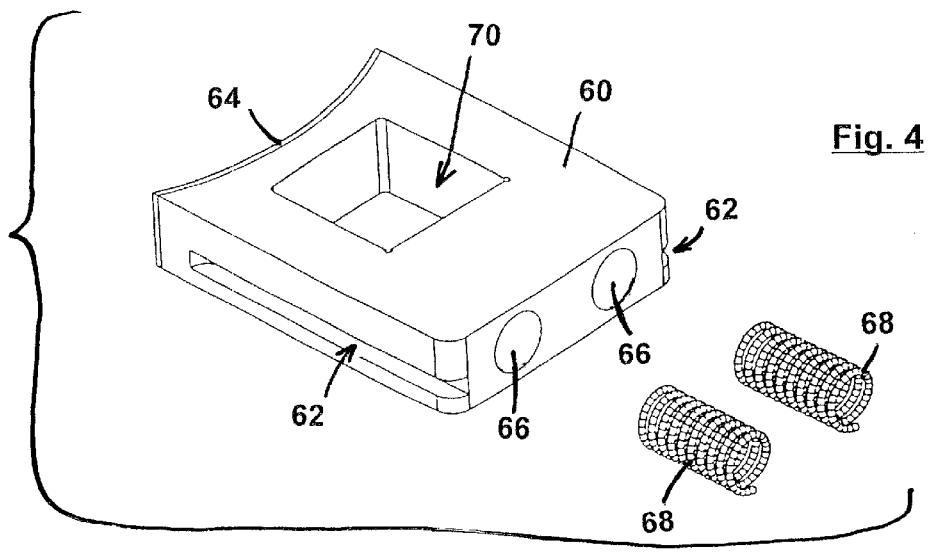
FIG. 4 is a perspective view illustrating a spring biased brake shoe for the brake assembly shown in FIG. 1.

FIG. 4 is a perspective view illustrating a spring biased brake shoe 60 for the brake assembly 30. Opposite sides of the brake shoe 60 preferably include grooves 62 for slidable engagement along the projecting ribs 52 of the base assembly 40. Thus, these ribs only allow generally linear movement of the brake shoe 60 with reference to the base 40. The brake shoe 60 also includes an arcuate face 64 contoured to generally match the curvature of the steering dial 16. Consequently, sliding the arcuate face 64 into contact with the steering dial 16 frictionally secures the dial in place. In a face opposite the arcuate face 64, the brake shoe 60 includes recesses, or projections, 66 that retain springs 68. Recesses or projections on the inner face of the end piece 46 of the base can also retain the springs 68, such that the springs are captive between the base 40 and the brake shoe 60. An upper face of the brake shoe 60 includes a recess or opening 70 that cooperates with an actuator arm 84 of the brake toggle 80, as described with reference to FIG. 5.

During operation, the brake shoe 60 moves either towards or away from the end piece 46. In a retracted ("brake off") position, the brake shoe 60 slides towards the end piece 46, and away from and out of contact with the steering dial 16. In an engaged ("brake on") position, the brake shoe 60 slides away from the end piece 46 towards, and into contact with the steering dial 16. Pressure is applied by the brake shoe 60 against the steering dial 16 sufficient to generate a frictional force capable of maintaining the steering dial 16 in position and thereby overcoming the resilience of the catheter shaft and fixing the shaft in any selected position. When the brake shoe 60 is engaged, the arcuate face 64 preferably locks the steering dial 16 to an extent sufficient to prevent freewheeling but permit the user to adjust the steering dial with moderate finger pressure. Because the steering dial 16 is generally circular, the matched curvature of the arcuate face 64 and the steering dial can secure the dial in an infinite number of positions throughout the entire range of motion of the catheter shaft.

To achieve dynamic locking, the brake assembly 30, in one form of the invention, comprises only the base assembly 46, the brake shoe 60, and at least one spring 68. Alternatively, the brake shoe 60 and the spring 68 are replaced by a spring-biased brake shoe. The springs 68 act in compression between the brake shoe 60 and the base 40, which biases the brake shoe 60 towards the engaged position. Hence, the arcuate face 64 maintains contact with the steering dial 16. As a user rotates the steering dial 16, the friction fit between the steering dial 16 and the arcuate face 64 hinder the catheter shaft 14 from moving after the dial is released. Thus, the catheter shaft 14 remains in a locked position.

Figure 5:
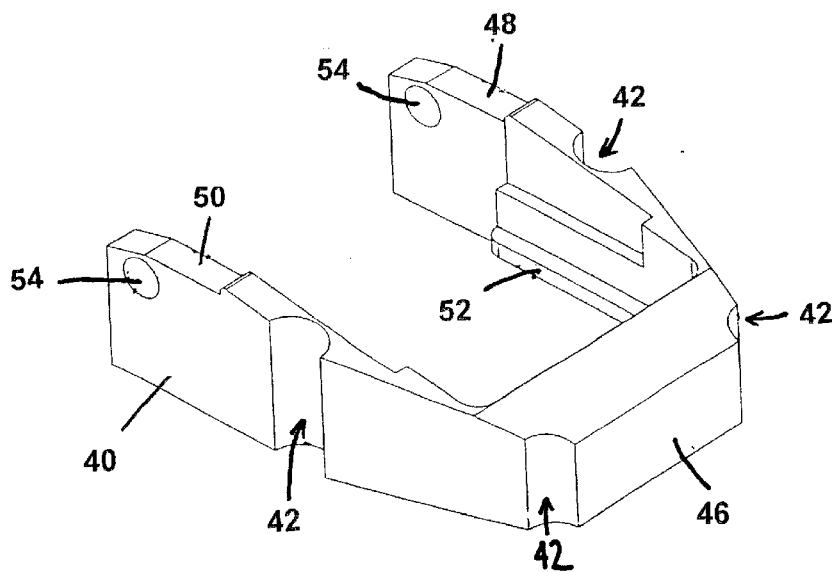
FIG. 5 is a perspective view illustrating a brake toggle for controlling the operation of the brake assembly of FIG. 1.
Figure 6:
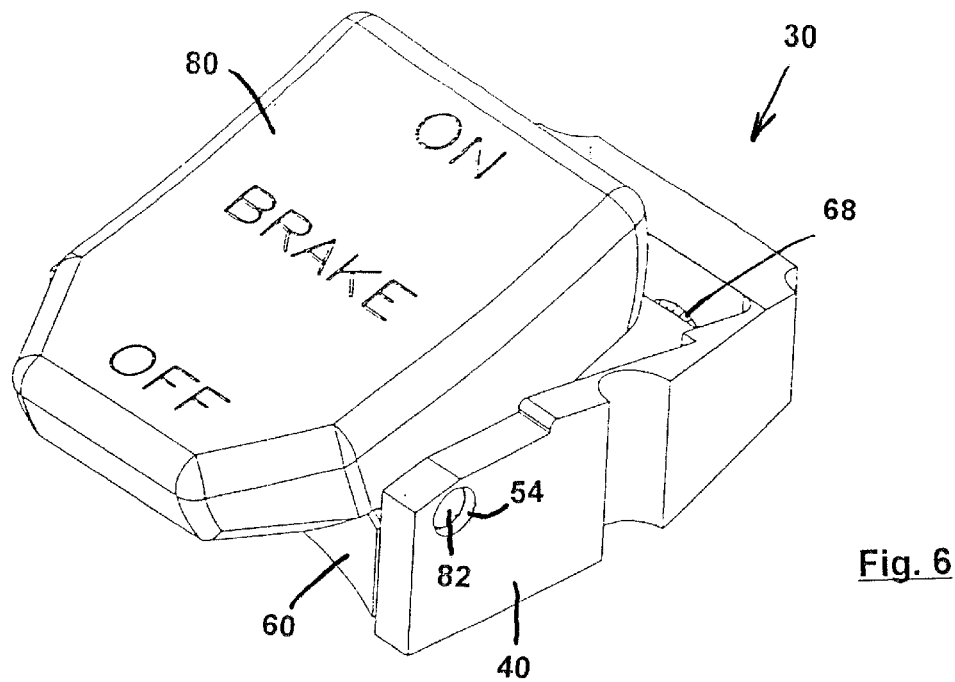
FIG. 6 is a perspective view illustrating the assembly of the brake shoe of FIG. 4 and the toggle of FIG. 5.
Figure 7:
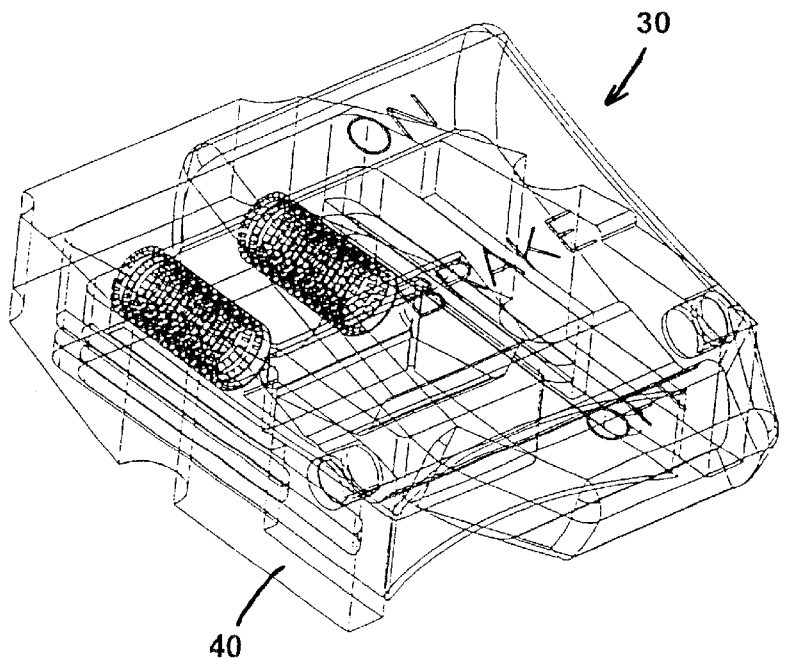
FIG. 7 is a perspective view of the brake assembly of FIG. 1 illustrating the position of the springs.

FIG. 5 is a perspective view illustrating a brake toggle 80 for controlling the operation of the brake assembly 30. The brake toggle 80 includes pivot lugs 82 that extend outwardly from opposite sides of this toggle. These lugs are engaged and pivotally mounted within the openings 54 of the first arm 48 and the second arm 50 (see FIG. 6) of the base assembly. Using pivotal mounting, the brake toggle 80 rock back and forth between an "on" position and an "off" position. The pivot lugs 82 are preferably positioned approximately midway along the length of the toggle 80, which facilitates an easy change of position. Typically, the brake toggle 80 will include labeling that indicates the on and off positions In addition to the pivot lugs 82, the toggle 80 includes an actuator arm 84 that extends from a lower face. A recess 70 in the brake shoe 60 receives the actuator arm 84. The actuator arm 84 acts as a cam to slide the brake shoe 60 away from the steering dial 16 into the retracted ("brake off") position. Generally, the actuator arm 84 moves in response to movement of the brake toggle 80. For example, moving the brake toggle 80 into its "off" position causes the actuator arm to move the brake shoe 60 out of contact with the steering dial 16. Consequently, the catheter shaft 14 becomes unlocked, which allows freewheeling. Moving the brake toggle 80 into the "on" position transfers control of the brake assembly 30 from the actuator arm 84 to the springs 68 (see FIG. 7). As mentioned above, the springs 68 bias the brake shoe 60 towards an engaged position. Thus, the spring(s) 68 drive the brake shoe 60 into contact with the steering dial 16, which locks the steering dial 16 to prevent freewheeling. The spring constant and compression distance of the spring(s) result in the application of a normal force between the shoe 60 and the dial 16, which together with the coefficient of friction between the shoe and dial, generates a frictional force sufficient to resist the resilience or memory of the shaft that would otherwise cause the shaft to return to a straight configuration.

The actuator arm 84 is normally self-locking. For example, putting the brake toggle 80 in an "on" position keeps the toggle 80 in that position until the user applies sufficient force to pivot it to the "off" position. In this manner, a user can put the brake toggle 80 into its "off" position for freewheeling operation of the steering dial 16. When the catheter shaft 14 is flexed to a desired position, the user then switches the brake toggle 80 into its "on" position, which locks the steering dial 16 to prevent freewheeling. Locking the steering dial 16 maintains the catheter shaft 14 in the desired flexure orientation until the brake is unlocked. Preferably, the user can adjust the shaft flexure when the brake is applied in the "on" position by application of moderate finger pressure to the steering dial sufficient to overcome the frictional force of the brake.

In view of the foregoing, it will be appreciated that the present invention provides a brake assembly 30 for locking a steerable catheter 10. By using the spring biased brake shoe 60, the brake assembly 30 can dynamically lock the catheter 10 in an infinite number of positions throughout the catheter shaft's range of motion. Using the toggle 80, the brake assembly 30 can switch from freewheeling operation to locked operation. These features result in freeing the user's steering hand to carry out other tasks.

Figure 8:
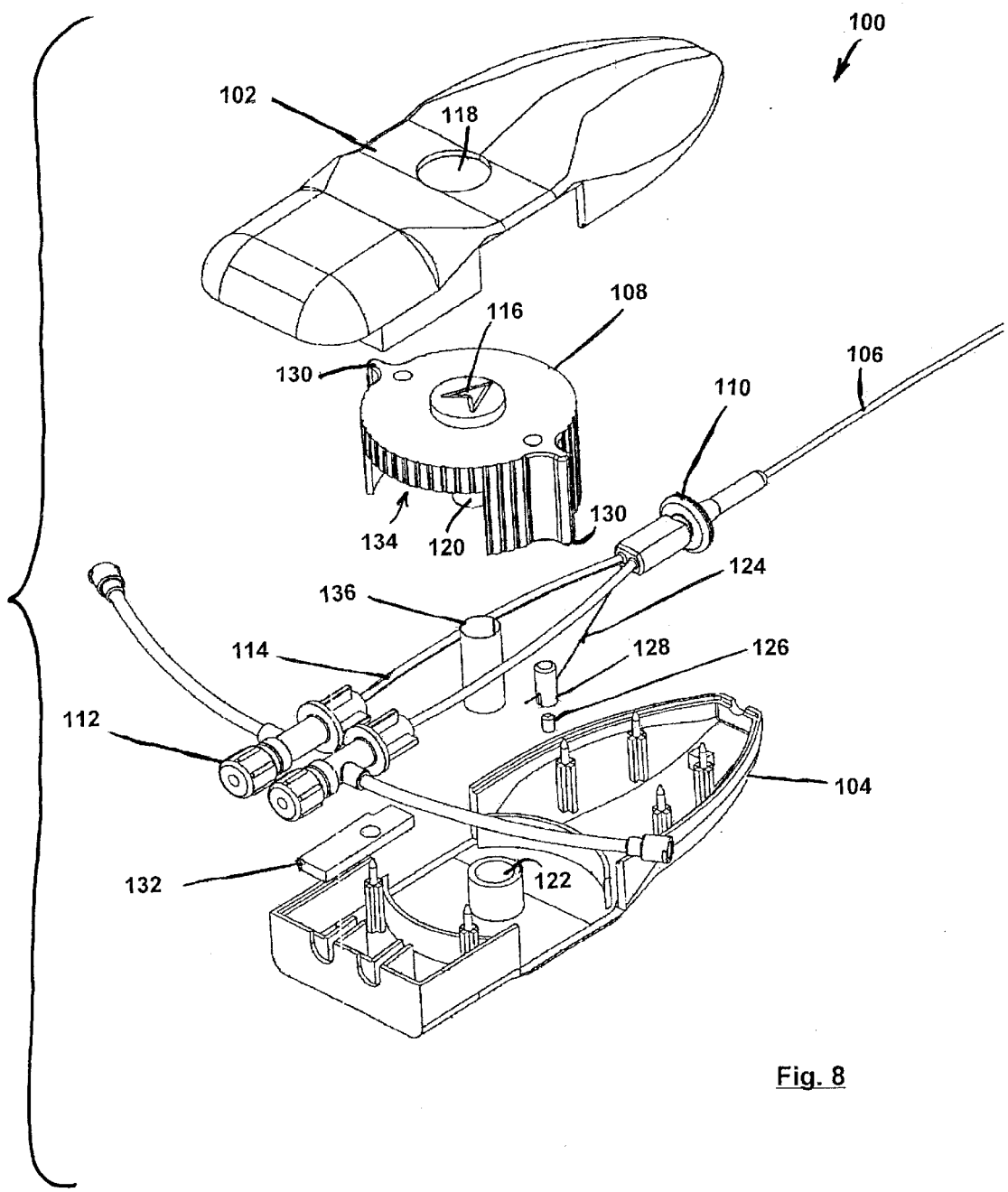
FIG. 8 is an exploded perspective view of another embodiment of the invention, according to preferred form.

FIG. 8 shows a catheter having a dynamic braking system according to another preferred form of the present invention. In this embodiment of the invention, the braking mechanism remains locked, and is not switchable to permit freewheeling of the steering dial. The catheter 100 preferably comprises a housing formed by upper and lower half housings 102, 104, a steerable flexible catheter shaft 106 defining one or more lumens extending through its length, and a rotationally mounted steering dial 108 for selectively controlling the flexure of the shaft. The shaft 106 is preferably mounted to a manifold 110 providing fluid communication with one or more inlet housings 112 via manifold extension tubes 114. The manifold 110 preferably comprises a mounting ring for engagement between the upper and lower half housings 102, 104 to secure the shaft 106 to the housing. One or more steering wires 124 extend through at least a portion of the shaft 106, whereby tension applied to the steering wire(s) causes flexure of the shaft. End(s) of the steering wire(s) are affixed to the steering dial 108, preferably by a set screw 126 engaged within an insert 128 attached to the steering dial a distance from the dial's axis of rotation.

The steering dial 108 preferably comprises an upper face having an outwardly projecting central hub 116 for rotational engagement within a cooperating recess or opening 118 provided in the upper half housing 102. The hub 116 preferably comprises a directional indicator for indicating the corresponding direction and degree of flexure of the shaft 106. The steering dial 108 preferably further comprises a generally cylindrical boss 120 projecting outwardly from a lower face thereof, opposite the hub 116, for rotational engagement within a cooperating socket 122 of the lower half housing 104. Assembly of the upper and lower half housings 102, 104 by coupling of crash pins or other attachment means captures the steering dial 108 within the housing and constrains the dial to rotation about an axis through the hub 116 and the boss 120. The steering dial 108 preferably comprises one or more wings 130 extending radially outward from a circumferential face of the dial and projecting externally of the housing for easier manipulation of the dial by a user. A stop 132 is optionally mounted to the housing and extends through a cutout section 134 of the circumferential face of the steering dial 108 to limit the extent of rotation permitted by the steering dial. The cutout section 134 is preferably sized to span an arc of a selected angle, such that the steering dial 108 cannot rotate beyond that selected angle due to contact between the stop 132 and the edges of the dial surrounding the cutout section. The cutout section can be located along the circumferential face of the steering dial 108 to permit steering of the shaft 106 in one direction only, to an equal extent in either direction, or to a greater extent in a first direction than in a second direction. In a preferred embodiment, the dial is permitted to steer in one direction only, and a single steering wire leg 124 is provided to effect steering in that direction. The resilience or "memory" of the shaft 106 biases the shaft to return to a straight orientation when tension is released from the single steering wire 124 by returning the dial to its neutral position.

Dynamic braking of the steering mechanism is accomplished by a brake assembly comprising a brake sleeve 136 frictionally engaged between the steering dial boss 120 and the socket 122 in the housing. The inner and outer diameters of the sleeve 136 form interference fits with the outer diameter of the steering disc boss 120 and the inner diameter of the socket 122, respectively. The tightness or degree of interference of these fits is selected to permit smooth rotation of the steering dial 108 by moderate finger pressure, and to produce friction sufficient to resist the tendency of the shaft 106 to return to a straight configuration as a result of the shaft material's memory. The brake sleeve 136 is preferably a split cylinder of metal, plastic or other material having sufficient rigidity and wear-resistance to maintain the frictional interference fits with the steering disc boss 120 and the socket 122 during the anticipated life of the catheter device, and having the desired coefficient of friction with the materials of the steering disc boss and the socket.

While the invention has been described in its preferred forms, it will be readily apparent to those of ordinary skill in the art that many additions, modifications and deletions can be made thereto without departing from the spirit and scope of the invention.

What is claimed is:

1. A steerable catheter, comprising;
   a catheter body;
   a flexible catheter shaft extending from the catheter body;
   a steering dial rotationally mounted to the catheter body for manipulating the shaft;
   a brake assembly, comprising:
      a brake shoe positioned in sliding relation to the base assembly and having a contact face slidably mounted to the catheter body for selectively engaging and disengaging with the steering dial; and
      at least one spring for biasing the contact face of the brake shoe against the steering dial,
   wherein actuation of the steering dial with the brake shoe engaged imparts flexure of the catheter shaft retains the catheter shaft in a flexed position upon release of the steering dial, and allows adjustment of the flexed position of the catheter shaft by further actuation of the steering dial with the brake shoe engaged; and wherein actuation of the steering dial with the brake shoe disengaged imparts flexure of the catheter shaft and releases the catheter shaft to an unflexed position upon release of the steering dial.

2. The steerable catheter of claim 1 further comprising a base assembly connected to the catheter body an positioned proximate the steering dial.

3. The steerable catheter of claim 1 further comprising a toggle pivotally connected to the base assembly and movable between a first position and a second position.

4. The steerable catheter of claim 3 wherein the toggle comprises an actuator arm for engagement with the brake shoe to retract the brake shoe out of contact with the steering dial when the toggle is in the second position.

5. The steerable catheter of claim 2 wherein the base assembly comprises a generally U-shaped yoke.

6. The steerable catheter of claim 2 wherein the base assembly comprises ribbed extensions for sliding engagement with cooperating channels of the brake shoe.

7. A steerable catheter comprising a housing, a flexible shaft extending from said housing, a toggle switch pivotally mounted to the housing and movable between a first position and a second position, a steering dial for steering said shaft, and a brake assembly, said brake assembly comprising a brake shoe linked to the toggle switch whereby when said toggle switch is in its first position the brake shoe is frictionally engaged with said steering disc and retains the shaft in a flexed position upon manipulation and release of the steering disc, and wherein movement of the toggle switch to its second position disengages the brake element from the steering disc and releases the shaft to an unflexed position.

8. The steerable catheter of claim 7 wherein said housing comprises a socket, and said steering dial comprises a boss for rotational engagement within said socket, and wherein said brake assembly comprises a brake sleeve frictionally engaged between the socket and the boss.

9. A steerable catheter comprising:
   a catheter body;
   a flexible catheter shaft extending from the catheter body;
   a steering actuator for imparting flexure to the catheter shaft, said steering actuator having a curved face;
   a brake assembly comprising a brake shoe with a curved face for selective engagement and disengagement with the curved face of the steering actuator, wherein engagement of the curved face of the brake shoe with the curved face of the steering actuator permits manipulation of the steering actuator to impart flexure to the catheter shaft and retain the catheter shaft in a flexed position, and wherein disengagement of the brake shoe from the steering actuator permits freewheeling of the steering actuator.

10. The steerable catheter of claim 9 the brake assembly locks the catheter shaft in any selected position within a continuous range.

11. The steerable catheter of claim 9 the brake assembly retains the catheter shaft in a flexed position by maintaining frictional contact between the brake shoe and the radiused face of the steering actuator.

12. The steerable catheter of claim 9, wherein the brake assembly further comprises a toggle and an actuator arm cooperating with the brake shoe to selectively engage and disengage the brake assembly with the steering actuator.

13. The steerable catheter of claim 9 wherein the catheter body comprises a gene ally U-shaped yoke.

14. The steerable catheter of claim 9 wherein the catheter body comprises ribbed extensions for sliding engagement with cooperating channels of the brake shoe.

* * * * *